United States Patent
Mohamed

(10) Patent No.: US 6,279,338 B1
(45) Date of Patent: Aug. 28, 2001

(54) COLD COMPRESSES APPARATUS

(76) Inventor: Samir Badry Mohamed, P.O. box 3612, Code No. 32067, Hawali (KW)

( * ) Notice: Subject to any disclaimer, the term of this patent is extended or adjusted under 35 U.S.C. 154(b) by 0 days.

(21) Appl. No.: 09/507,783

(22) Filed: Feb. 19, 2000

(51) Int. Cl.$^7$ ............................. F25D 23/12; A61F 7/00
(52) U.S. Cl. .................... 62/259.3; 165/46; 607/104
(58) Field of Search ........................ 62/259.3, 406, 62/457.1, 530, 424; 165/46; 607/86, 99, 104, 108, 109

(56) References Cited

U.S. PATENT DOCUMENTS

| | | | |
|---|---|---|---|
| 4,259,961 | * | 4/1981 | Hood, III . |
| 4,691,762 | * | 9/1987 | Elkins et al. .............................. 165/46 |
| 5,344,436 | * | 9/1994 | Fontenot et al. .................... 165/46 X |
| 5,417,720 | * | 5/1995 | Mason . |
| 5,456,701 | * | 10/1995 | Stout .................................. 165/46 X |
| 5,507,792 | * | 4/1996 | Mason et al. .......................... 607/104 |
| 5,755,275 | * | 5/1998 | Rose et al. .............................. 165/46 |

* cited by examiner

Primary Examiner—William Doerrler
Assistant Examiner—Chen-Wen Jiang

(57) ABSTRACT

A cold compresses apparatus comprises a bladder used for cooling the forehead and/or the limbs of the feverish patient to reduce his temperature. The bladder is cooled by passing cold air inside it. The source of cold air is an air cooling unit containing a thermostat to control the cooling temperature of the outer surface of the bladder. The air-cooling unit works by electric power.

13 Claims, 1 Drawing Sheet

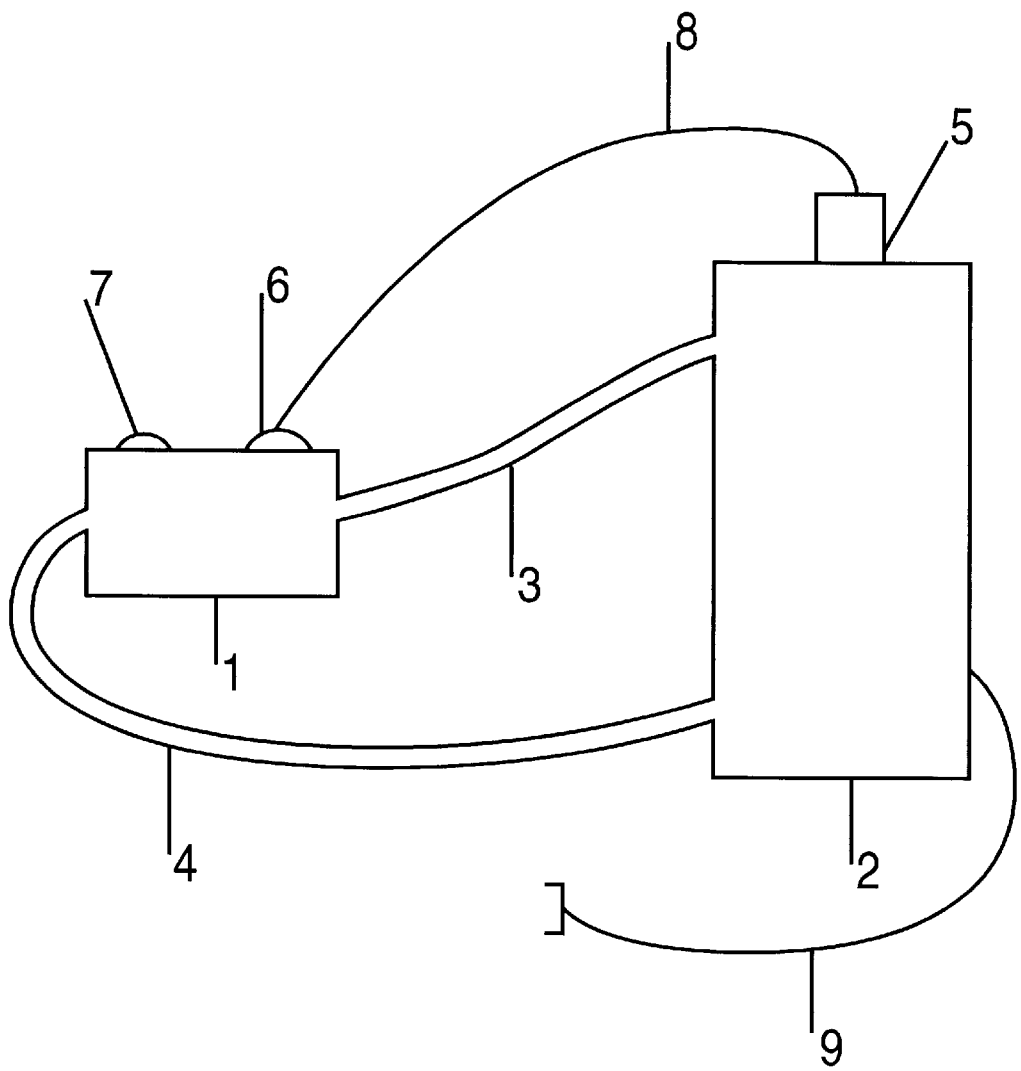

COLD COMPRESSES APPARATUS

BACKGROUND OF THE INVENTION

This invention is in the medical field. During treatment of fever, making cold compresses (cold fomentations) is frequently required. The usual method is by using a piece of cloth, gauze or towel put in cold water and put on patient's forehead or limb. This method is annoying to the patient because it wets the patient and his clothes, and also the sudden touch of the cold object also annoys the feverish patient. Another method is by using bag containing ice; also water vapour condenses on the ice bag which becomes wet. These problems can be solved by this invention which depends on usage of a rubber bladder (bag) which is cooled by passing cold air inside it. This bladder is used to make cold compresses (cold fermentations) to the patient. This method is easy and dry, and also the bladder is put on the patient's forehead or limb first and then gradually cooled so not annoying the feverish patient by sudden touch of cold object.

The cold air depending apparatus is easy to manufacture, may be not expensive, light, and if leakage occurred from the apparatus; leakage of air is less problematic than leakage of fluid or form.

BRIEF SUMMARY OF THE INVENTION

This apparatus consists of a bladder (or a bag) made of rubber (or any other suitable material), this bladder is connected to two rubber tubes. The two rubber tubes connected to the bladder are; one input tube that conducts cold air from an air cooling unit to the bladder, and the other is an output tube that conducts air from the bladder to the air cooling unit to be cooled again. The air cooling unit is an air conditioning unit like those used in houses or cars but of small suitable size. The air cooling unit contains also a fan for making air circulate in the tubing and contains a thermostat to control the temperature of the outer surface of the bladder. The thermostat sensor and a thermometer are connected to the outer surface of the bladder. The bladder is put on the patient's forehead or wrapped around the patient's limb to lower his temperature after cooling the bladder.

The advantages of this invention is that it is easy to manufacture, not much expensive, is ready to use (does not need preparation as in case of usual cold fomentations), does not wet the patient or his clothes, the bladder is put on the patient first and then gradually cooled so not annoying him by sudden touch of cold object, the cooling temperature of the apparatus is adjustable and well—controlled and stabilized by the thermostat, the apparatus is suitable for home or hospital use, can be used by the patient alone without assistance, the cooling unit can be connected to 5 bladders (one on the forehead and one for each limb of the patient) for more rapid and effective procedure, the apparatus is of small size and weight, no problems if leakage occurs unlike in case of using fluid or foam to circulate in the tubing.

BRIEF DESCRIPTION OF THE SEVERAL VIEWS OF THE DRAWING.

The present FIGURE shows the invention.

DETAILED DESCRIPTION OF THE INVENTION

This invention is used for making cold compresses (cold fomentations) to the feverish patient to reduce his temperature. The idea is putting a cold bladder (bag) made of rubber or any other suitable material on the patient's forehead and/or around his limb(s) to reduce his temperature. The bladder is cooled by passing cold air inside it. The source of cold air is an air cooling unit which is an air conditioner like that used in houses and in cars but it is of a small suitable size. The cold air is conducted from the air cooling unit to the bladder by an input rubber tube, the air in the bladder is conducted to the air cooling unit to be cooled again by an output rubber tube. The air cooling unit contains a fan to make air circulate in the tubes and bladder. The air cooling unit contains a thermostat to control (adjust and fix) the temperature of the outer surface of the bladder. The sensor of the thermostat is connected to the outer surface of the bladder. Also, a thermometer is connected to the outer surface of the bladder. The cooling unit works by electric power. So, as appears in the included drawing, this apparatus consists of; bladder, input tube, output tube, air cooling unit (containing fan and thermostat) and a thermometer.

The cooling unit can be connected to one or more than one bladder e.g. 5 bladders one for forehead and 4 for the 4 limbs of the patient for more rapid and effective cooling action.

What is claimed is:

1. A cold compresses apparatus comprising:
   a bladder through its cavity circulates cold air;
   an air-cooling unit as a source for said cold air;
   an input and an output tubes connecting said bladder cavity to said air-cooling unit;
   a temperature sensor;
   a thermostat to control and fix the temperature of the outer surface of said bladder;
   a fan in said air-cooling unit to make said cold air circulates in said bladder.

2. The cold compresses apparatus according to claim 1, wherein said cavity is rectangular in shape.

3. The cold compresses apparatus according to claim 1, wherein said air-cooling unit further comprising electric power source.

4. The cold compresses apparatus according to claim 1, wherein said input tube is made of rubber and conducting the cold air from said air-cooling unit to the cavity of said bladder.

5. The cold compresses apparatus according to claim 1, wherein said output tube is made of rubber and conducting air from the cavity of said bladder to said air-cooling unit to be re-cooled.

6. The cold compresses apparatus according to claim 1, wherein said temperature sensor is connected to the outer surface of said bladder to sense the temperature.

7. The cold compresses apparatus according to claim 1, wherein said thermostat is connected to said temperature sensor and to said air-cooling unit.

8. The cold compresses apparatus according to claim 1, wherein said thermostat controls and fixes the temperature of the outer surface of said bladder.

9. The cold compresses apparatus according to claim 1, wherein said thermostat includes a switch to set it to a wanted temperature.

10. The cold compresses apparatus according to claim 1, wherein said thermometer is connected to the outer surface of said bladder.

11. The cold compresses apparatus according to claim 1, wherein the circulation of said cold air inside the cavity of said bladder makes said bladder cold.

12. The cold compresses apparatus according to claim 1, wherein circulation of said cold air in the apparatus is in the form of a closed circulation.

13. The cold compresses apparatus according to claim 1, wherein said thermostat controls and fixes the temperature of the outer surface of said bladder.

* * * * *

UNITED STATES PATENT AND TRADEMARK OFFICE
CERTIFICATE OF CORRECTION

PATENT NO.    : 6,279,338 B1
DATED         : August 28, 2001
INVENTOR(S)   : Mohamed, Samir Badry It is certified that error appears in the above-identified patent and that said Letters Patent is hereby corrected as shown below:

<u>Column 1,</u>
Line 15, delete "fermentations" and insert -- fomentations --
Line 23, delete "form" and insert -- foam --

Delete column 1, line 60 - column 2, line 18, and replace with
-- Detailed Description of the Invention
   This invention is used for making cold compresses (cold fomentations) to the feverish patient to reduce his temperature. The idea is putting a cold bladder 1 (bag) made of rubber or any other suitable material on the patient's forehead and/or around his limb(s) to reduce his temperature. The bladder 1 is cooled by passing cold air inside it. The source of cold air is an air-cooling unit 2 which is an air conditioner like that used in houses and in cars but it is of a small suitable size. The cold air is conducted from the air-cooling unit 2 to the bladder 1 by an input rubber tube 3, the air in the bladder 1 is conducted to the air-cooling unit 2 to be cooled again by an output rubber tube 4. The air-cooling unit 2 contains a fan to make air circulate in the tubes and bladder. The air-cooling unit 2 contains a thermostat 5 to control (adjust and fix) the temperature of the outer surface of the bladder 1. The sensor 6 of the thermostat is connected to the outer surface of the bladder 1. A wire 8 for thermostat connects the sensor 6 of the thermostat to the thermostat 5. Also, a thermometer 7 is connected to the outer surface of the bladder 1. The air-cooling unit 2 works by electric power (a wire 9 is for power supply). So, as appears in the included drawing, this apparatus consists of; bladder 1, input tube 3, output tube 4, air-cooling unit 2 (containing a fan and a thermostat 5) and a thermometer 7.
   The air-cooling unit 2 can be connected to one or more than one bladder e.g. five bladders one for forehead and four for the four limbs of the patient for more rapid and effective cooling action. --

Signed and Sealed this

Sixteenth Day of July, 2002

Attest:

*Attesting Officer*

JAMES E. ROGAN
*Director of the United States Patent and Trademark Office*